US011650326B2

(12) United States Patent
Somero et al.

(10) Patent No.: US 11,650,326 B2
(45) Date of Patent: May 16, 2023

(54) ADAPTIVE ANTENNA ARRANGEMENT FOR WEARABLE TRAINING COMPUTER

(71) Applicant: Polar Electro Oy, Kempele (FI)

(72) Inventors: Vesna Somero, Kempele (FI); Ville Majava, Kempele (FI); Pertti Nissinen, Kempele (FI); Atte Kuosmonen, Kempele (FI); Marko Tuhkala, Kempele (FI)

(73) Assignee: Polar Electro Oy, Kempele (FI)

( * ) Notice: Subject to any disclaimer, the term of this patent is extended or adjusted under 35 U.S.C. 154(b) by 274 days.

(21) Appl. No.: 16/942,533

(22) Filed: Jul. 29, 2020

(65) Prior Publication Data

US 2021/0063581 A1 Mar. 4, 2021

(30) Foreign Application Priority Data

Aug. 28, 2019 (EP) ..................................... 19194074

(51) Int. Cl.
*G01S 19/19* (2010.01)
*G01S 19/39* (2010.01)
(Continued)

(52) U.S. Cl.
CPC .............. *G01S 19/19* (2013.01); *G01S 19/26* (2013.01); *G01S 19/396* (2019.08); *G01S 19/47* (2013.01); *H01Q 1/273* (2013.01)

(58) Field of Classification Search
CPC ........ G01S 19/19; G01S 19/396; G01S 19/26; G01S 19/47; H01Q 1/24; H01Q 1/273;
(Continued)

(56) References Cited

U.S. PATENT DOCUMENTS 9,943,744 B2 * 4/2018 Meadows .......... G09B 19/0038
10,871,751 B2 * 12/2020 Yun ...................... H01Q 9/0464
(Continued)

FOREIGN PATENT DOCUMENTS

| CN | 102023301 A | 4/2011 |
| CN | 106711613 A | 5/2017 |
| FR | 2 780 187 A1 | 12/1999 |

OTHER PUBLICATIONS

First Office Action received for Chinese Patent Application Serial No. 202010862932.2 dated May 28, 2021, 9 pages. (Including English Translation).
(Continued)

*Primary Examiner* — Erin F Heard
*Assistant Examiner* — Kenneth W Good
(74) *Attorney, Agent, or Firm* — Fisherbroyles, LLP (57) ABSTRACT

A wearable training computer includes a global navigation satellite system (GNSS) antenna arrangement configured to provide a group of antenna configurations for receiving a GNSS signal, wherein each antenna configuration provides different radio frequency properties. The wearable training computer further includes a measurement circuitry configured to measure performance of the GNSS antenna and a processing circuitry configured to select, based on at least an activity type of a user of the wearable training computer, a subset of the antenna configurations from the group of the antenna configurations, and further configured to select, from the subset of the antenna configurations based on the measured GNSS antenna performance, an antenna configuration for receiving the GNSS signal.

15 Claims, 4 Drawing Sheets

(51) Int. Cl.
   *G01S 19/26* (2010.01)
   *G01S 19/47* (2010.01)
   *H01Q 1/27* (2006.01)
(58) Field of Classification Search
   CPC ..... A61B 5/00; A61B 5/02438; A61B 5/1118; A61B 5/11
   See application file for complete search history.

(56) References Cited

U.S. PATENT DOCUMENTS

| | | | | |
|---|---|---|---|---|
| 10,998,615 | B1* | 5/2021 | van Erven | G06F 3/165 |
| 11,311,777 | B2* | 4/2022 | Yun | A61B 5/1118 |
| 2007/0188380 | A1* | 8/2007 | Duong | G01S 19/28 |
| | | | | 455/277.1 |
| 2008/0157961 | A1* | 7/2008 | Park | G06Q 10/08 |
| | | | | 340/540 |
| 2008/0303729 | A1* | 12/2008 | Milosavljevic | H01Q 21/28 |
| | | | | 343/722 |
| 2012/0130201 | A1* | 5/2012 | Jain | A61B 5/08 |
| | | | | 600/301 |
| 2014/0372026 | A1* | 12/2014 | Georgy | G01S 19/47 |
| | | | | 701/469 |
| 2016/0054449 | A1* | 2/2016 | Pekonen | A61B 5/1112 |
| | | | | 342/357.57 |
| 2018/0329075 | A1* | 11/2018 | Wu | G01S 19/42 |
| 2019/0067803 | A1* | 2/2019 | Kang | G04R 60/06 |
| 2019/0343429 | A1* | 11/2019 | Elhawary | A61B 5/6823 |
| 2021/0242598 | A1* | 8/2021 | Varjonen | H01Q 5/328 |

OTHER PUBLICATIONS

Extended European Search received in EP Patent Application No. 19194074.1 dated Feb. 17, 2020, 9 pages.

Second Office Action received for Chinese Patent Application Serial No. 202010862932.2 dated Jan. 4, 2022, 10 pages Including English Translation.

* cited by examiner

ADAPTIVE ANTENNA ARRANGEMENT FOR WEARABLE TRAINING COMPUTER

CROSS-REFERENCE TO RELATED APPLICATION

This application claims benefit and priority to European Application No. 19194074.1, filed Aug. 28, 2019, which is incorporated by reference herein in its entirety.

FIELD

The present invention relates to a field of wearable training computers, especially antenna arrangements of the wearable training computers.

SUMMARY

A global navigation satellite system, GNSS, is widely used in the wearable training computers nowadays for providing position, navigation and tracking information. An antenna is an essential part of the GNSS. Traditionally GNSS antennas are disposed in devices at locations that have a good exposure to GNSS signals. In wearable training computer, body motion, training gear, or clothing may hinder this exposure. Hence, a more sophisticated solution for the GNSS antenna of the wearable training computer is needed to improve the performance of the GNSS antenna in varying use cases.

The present invention is defined by the subject matter of the independent claim.

Embodiments are defined in the dependent claims.

The embodiments and features, if any, described in this specification that do not fall under the scope of the independent claim are to be interpreted as examples useful for understanding various embodiments of the invention.

BRIEF DESCRIPTION OF THE DRAWINGS

In the following the invention will be described in greater detail by means of preferred embodiments with reference to the attached drawings, in which.

DETAILED DESCRIPTION

The following embodiments are exemplifying. Although the specification may refer to "an", "one", or "some" embodiment(s) in several locations of the text, this does not necessarily mean that each reference is made to the same embodiment(s), or that a particular feature only applies to a single embodiment. Single features of different embodiments may also be combined to provide other embodiments.

Embodiments of the invention relate to a wearable training computer configured to carry out measurements during a physical exercise performed by a user. The wearable training computer may be a portable system attachable to the user's body. The wearable training computer is configured to measure physiological training data from the user's performance during the physical exercise and to output the training data to the user via a user interface of the training computer and/or via a user interface of another apparatus. The wearable training computer may further comprise an apparatus configured to be attached to the object. Such an apparatus may comprise an attachment structure designed and arranged to receive the training computer in a fixed, integrated, or detachable manner and to attach the training computer to the object. The attachment may be realized by a band that may be designed to encircle the object such that the band is attached around the object. The band may comprise locking parts at ends of the band where the locking parts form mutually counterparts such as a buckle and a catch. The locking parts may fix the band around the object as is commonly known in the field of wristwatches, wrist computers etc. Other forms of attachment of wearable devices are equally possible, e.g. the training computer may be integrated or attached to a garment such as a shirt, show, or harness. In other embodiments, the attachment structure may be arranged to attach the apparatus to the device such as the bicycle. In such embodiments, the apparatus may be or may be comprised in a bike computer, for example.

The wearable training computer may comprise a global navigation satellite system, GNSS, to provide location, navigation and/or tracking capabilities for the wearable training computer. The wearable training computer using the GNSS comprises a GNSS antenna used for communicating with GNSS satellites. In conventional implementations such as vehicular navigators, the GNSS antenna is provided at a location with constant exposure to GNSS signals and, in such implementations, the GNSS antenna remains at the same location relative to the object/vehicle to which it is attaches. With wearable training computer, the user moves during physical activities, thus changing the relative position between the GNSS antenna and the object to which it is attached, i.e. the human body. The GNSS antenna may thus be shadowed by the user's body parts, training equipment, training clothes, etc. Hence, the GNSS antenna system that is capable to adapt to the different use cases is needed to improve the GNSS antenna performance.

According to an aspect, there is provided a wearable training computer, comprising: a global navigation satellite system, GNSS, antenna arrangement configured to provide a group of antenna configurations for receiving a GNSS signal, wherein each antenna configuration provides different radio frequency properties; a measurement circuitry configured to measure performance of the GNSS antenna; and a processing circuitry configured to select, based on at least an activity type of a user of the wearable training computer, a subset of the antenna configurations from the group of the antenna configurations, and further configured to select, from the subset of the antenna configurations based on the measured GNSS antenna performance, an antenna configuration for receiving the GNSS signal.

Figure 1:
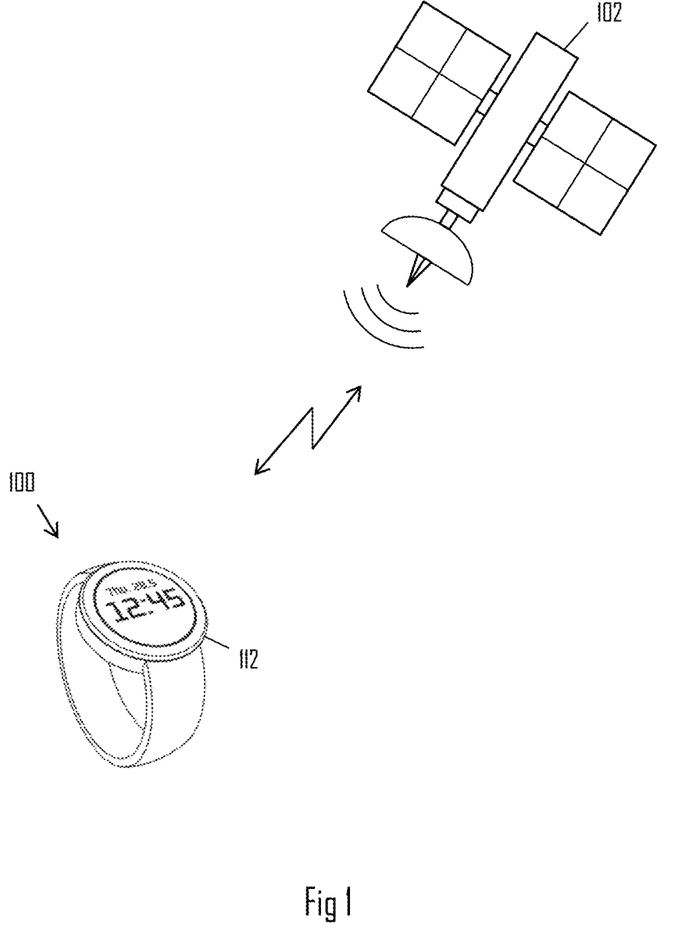
FIG. 1 illustrates a wearable training computer with a GNSS according to an embodiment of the invention.
Figure 2:
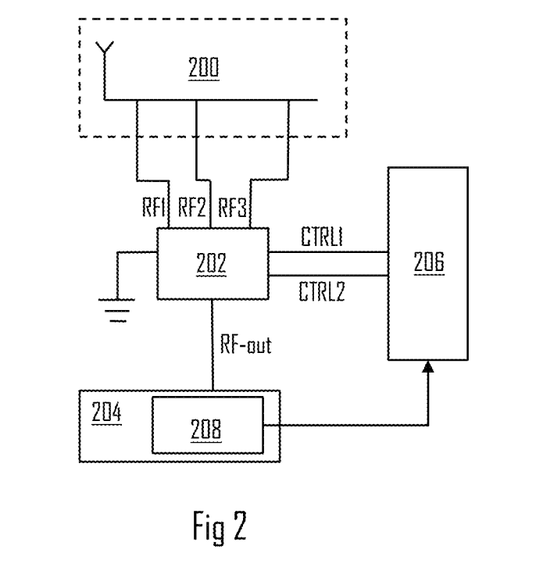
FIG. 2 illustrates a wiring diagram of a GNSS antenna according to an embodiment of the invention.

Referring to FIG. 2, wherein the wearable training computer with a GNSS signal reception capabilities is illustrated. In an embodiment, the wearable training computer 100 comprises a GNSS receiver 204, the antenna arrangement 200 configured to provide the group of the antenna configurations for the GNSS receiver 204, a measurement circuitry 208 and a processing circuitry 206. The GNSS signals may be transmitted by GNSS satellites such as a satellite 102 illustrated in FIG. 1. Only one satellite 102 is illustrated in FIG. 1 but the wearable training computer 100 with the GNSS capabilities may utilize a plurality of satellites to provide location, navigation and/or tracking information during the physical activities of the user of the wearable training computer 100.

In an embodiment, the antenna arrangement comprises the group of alternative antenna configurations, wherein the group comprises a plurality of the antenna configurations having different radio frequency (RF) properties. Each antenna configuration may provide a unique combination of one or more of the following RF properties: antenna gain, (main) beam direction or axial ratio, and polarization or polarization isolation. The different RF-properties make possible to find out the optimal antenna configuration for the different use cases of the wearable training computer. For example, an orientation and a position of the wearable training computer in relation to the user's body may vary when the wearable training computer is in use during the activity, thus changing the antenna performance. A plurality of the antenna configurations with the different RF-properties make it possible to find out the optimal antenna configuration for the different orientations and positions of the wearable training computer. This enables an optimal connection between the wearable training computer and satellite during the activity despite the changing circumstances of the activity.

In an embodiment, the different RF-properties of the antenna configurations may be achieved, for example, by adjusting a power gain of the antenna, an axial ratio of the antenna and/or a polarization isolation of the antenna. In an embodiment, the adjusting maybe done mechanically by one or more solid state switches or tuners, passive RF-components, antenna connection points and/or reflectors. In another embodiment, adjusting may be done software basis, for example by a GNSS and/or MCU (microcontroller) software. In some case, the RF-properties of the antenna configurations may be adjusted mechanically and software basis.

FIG. 2 further illustrates an example of a wiring diagram of the antenna arrangement according to an embodiment. The wiring diagram comprises the GNSS antenna 200 and a RF switch 202. In addition, there is illustrated three RF contact points RF1, RF2, RF3 between the antenna 200 and RF switch 202, a RF-out line between the RF-switch 202 and the GNSS receiver 204 and also a first and a second control line CTRL1, CTRL2 between the processing circuitry 206 and the RF-switch 202.

Figure 3:
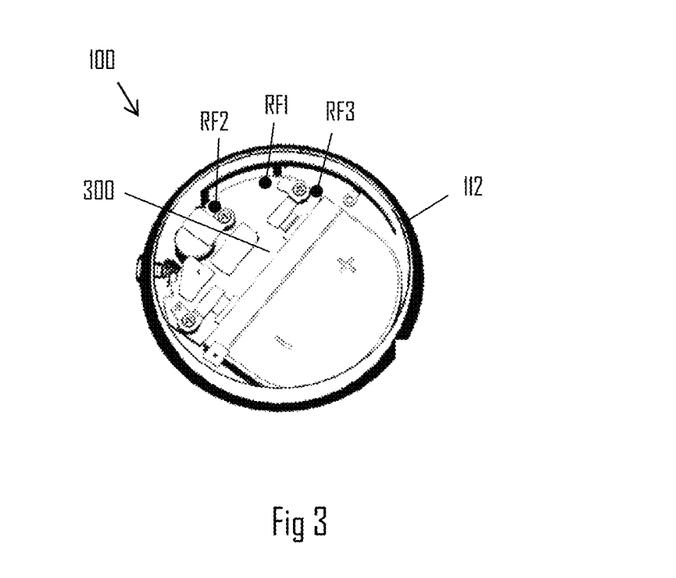
FIG. 3 illustrates RF-contact points according to an embodiment of the invention.

Referring to FIG. 3, in an embodiment, a printed wired board (PWB) 300 inside the wearable training computer 100 comprises three RF-contact points RF1, RF2, RF3. A structure of the wearable training computer is open in FIG. 3, such that the PWB and RF-contact points inside are visible. Also a casing 112, where the PWB is mounted is illustrated. In an embodiment where the wearable training computer is a wristwatch, the casing 112 may comprise a bezel that may be used as a part of the GNSS antenna 200.

In some embodiments, there are less or more than three RF-contact points.

The RF switch 202 may be configured, under the control of the processing circuitry 206, to couple the RF-contact points interchangeably to the GNSS receiver 204, the ground, or to an open state, depending on the desired RF properties of the GNSS antenna. The coupling of an RF contact point to the GNSS receiver may equally be called coupling the RF contact point to an antenna feed because the antenna feed typically refers to coupling the antenna with a transmitter/receiver, in this case the GNSS receiver. In an embodiment, the three RF-contact points are used and each of the points can be connected with the antenna feed, ground or it can be open. Hence, all combinations of the three RF-contact points formed with the antenna feed, ground or open state are possible to carry out to get desired RF-properties. In other words, the any of the three RF-contact points may have the antenna feed, it may be grounded or it may be open according to the desired antenna performance. In some embodiment, the antenna feed may be connected with a plurality of the RF-contact points at the same time. An RF contact point being open may be understood that the contact point is coupled to a signal line that is open-ended or substantially open-ended. Substantially open-ended may mean that there is a small capacitor, e.g. 1 pF, or a similar component at the open end, thus effectively terminating the RF contact point at the open end.

In an embodiment, the first RF-contact point RF1 is open, the antenna feed is in the second RF-contact point RF2 and the third RF-contact point RF3 is open.

In an embodiment, the antenna feed is in the first RF-contact point RF1, the second RF-contact point RF2 has an inductance, for example, 4.2 nH and the third RF-contact point RF3 is open.

With the three contact points at the different locations of the GNSS antenna, at least three different antenna configurations with different RF properties can be established. Further antenna configurations may be realized by implementing further contact points and/or coupling, by the switch 202 under the control of the processing circuitry 206, the contact points to various active and/or passive RF components that affect the RF properties.

Referring to FIG. 1, the wearable training computer comprises the measurement circuitry for measuring the GNSS antenna performance. The measuring may be, for example, a continuous process for defining the performance of the GNSS antenna. There may be, for example, a predetermined timing when the measurement is performed. The measurement may be performed periodically, for example once per second. In some embodiments, the measurement is not performed continuously. Hence, the measurement may be predetermined such that the measurement is performed according to a preset criterion. For example, the measurement may be performed when the orientation or position of the wearable training computer is changed, because the change may also affect the antenna performance. There may not be a need to measure the antenna performance if the orientation and/or position of the wearable training computer does not change in relation to the user's body, provided that the selected antenna configuration provides an acceptable GNSS signal quality. The performance measurement provides data on the signal quality between the antenna and satellite. The measurement data, provided by the measurement circuitry 208, is used by the processing circuitry 206 to define whether the GNSS antenna performance is acceptable or shall the antenna configuration be changed.

The activity type may refer to a sports type the user of the wearable training computer is performing or about to perform. The use case also refers to the activity/sports type and it may also refer to the orientation, position or movement of the wearable training computer during the particular activity or sports. The orientation, position and movement of the wearable training computer in relation to the user's body may be different in the different activities. Therefore, an antenna configuration optimal for one activity type may not provide acceptable performance for another activity type. It is also possible that some antenna configurations are acceptable for many activity types. Anyway, the activity type is an essential information when selecting the GNSS antenna configuration and, as a consequence, the processing circuitry 206 may use the activity type or sports type in the selection of the GNSS antenna configuration.

The wearable training computer provides the group of the antenna configurations having different RF-properties for the different use cases of the training computer. In an embodiment, the group of the antenna configurations is divided the subsets based on the activity type. Hence, a plurality of subsets of the antenna configurations may be formed from the group of antenna configurations. The each subset may be customised for a certain activity type. One antenna configuration may also be in several subsets, if it is suitable for the many activity types. The subset may comprise a plurality of the antenna configurations from which the antenna configuration is selected during the physical activity. A number of antenna configurations in the subset may vary and it may vary also between the different subsets. For example, an activity type associated with low and possibly periodic motion of the training computer, e.g. running, may have fewer antenna configurations in its subset than an activity type associated with high and unpredictable motion, e.g. hockey.

Figure 4:
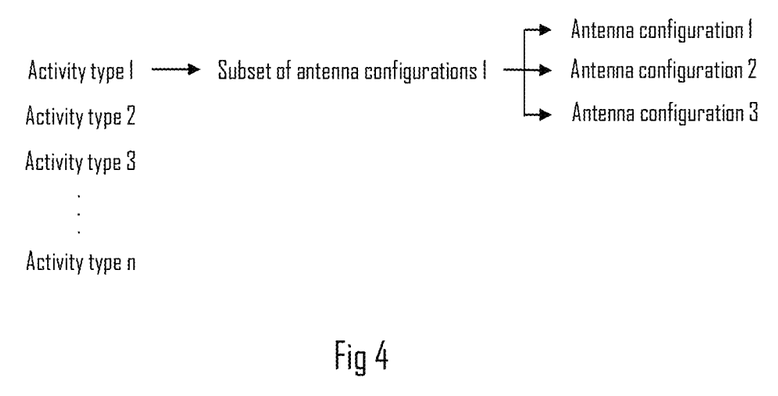
FIG. 4 illustrates a selection of subsets of antenna configurations according to an embodiment of the invention.

FIG. 4 illustrates an embodiment wherein the subsets of antenna configurations are formed based on the activity type. The activity type 1 comprises the subset of the antenna configurations 1 and the subset comprises three antenna configurations having different RF-properties, as described above. As illustrated in FIG. 4, the subset of antenna configurations 1 comprises three different antenna configurations but subset 2 may comprise, for example, five different antenna configurations (not illustrated in FIG. 3). Also, for example, antenna configuration 1 may be allocated to multiple subsets. The subsets may be formed during a design and/or testing stage of the training computer and stored in a memory of the training computer.

In an embodiment, the selection of the antenna configuration is carried out by the processing circuitry 206 based on the GNSS antenna performance measurement. The measurement circuitry 208 measures the GNSS antenna performance and based on the measurement data the processing circuitry selects the antenna configuration from the subset of the antenna configurations associated with the current activity type. Hence, the preselection of the antenna configurations (subset) is done based on the activity type and the selection of one of the antenna configurations in the subset based on the actual antenna performance (measurement). In an embodiment, the measurement circuitry measures performance of all antenna configurations of the selected subset and selects the configuration that is the most optimal. In such an embodiment, the processing circuitry may trigger a measurement phase where the processing circuitry cycles through all the antenna configurations of the subset to carry out the measurements for all antenna configurations of the subset.

Because the selection of the antenna configuration is done based on the actual real-time measurement, the antenna system is adaptive for different circumstances. The adaptive antenna system ensures that the optimal antenna configuration is in use during the physical activity of the user.

In an embodiment, the antenna configuration may also be selected from another subset that selected based on the activity type. Referring to FIG. 4, the subset of the antenna configuration 1 is selected based on the activity type but still it is possible to select, for example, the antenna configuration 4 that may be in the second subset if it seems to be optimal. Hence, the selected subset may not limit the selection of the antenna configuration. A use case could be that none of the antenna configurations provides an acceptable performance. In such a case, the processing circuitry may select an antenna configuration that is not in the subset associated with the current activity type and configure the measurement circuitry to measure the performance of the newly selected antenna configuration. In this manner, the subset is not binding to the processing circuitry in such exceptional situations.

In an embodiment, in addition to the activity type, also other characteristics may be used in the antenna configuration selection. Such other characteristics may include user parameters received as an input from the user. For example, whether user parameters indicate that the wearable training computer is used in a left hand or a right hand of the user or is it worn elsewhere may be used as an input to the selection of the antenna configuration or the selection of the subset(s). In an embodiment, the wearable training computer may automatically recognize how and where it is worn, for example, is it in the left or right hand. In another embodiment, the user may feed into the system how the wearable training computer is worn and used. It is also possible that the manual feeding by the user and automated recognition is combined. The processing circuitry may ask through a user interface of the training computer the user to confirm, for example, that the training computer is currently in the right hand.

Figure 5:
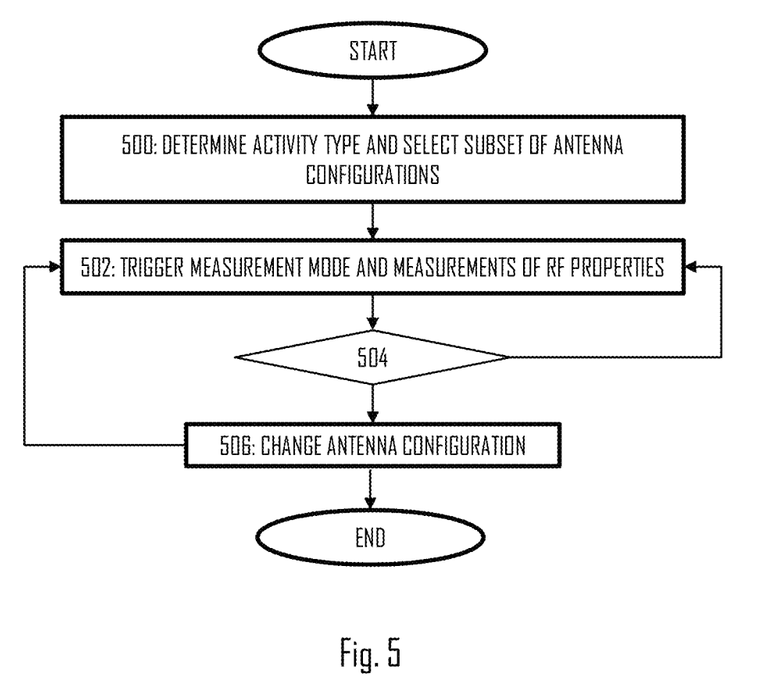
FIG. 5 illustrates a process for adaptive selection of antenna configurations during physical activities according to an embodiment of the invention.

The next embodiment illustrated in FIG. 5 describes how the adaptive GNSS antenna arrangement may be applied to the wearable training computer. At first the activity type is fed into the system and the subset of antenna configurations is selected, by the processing circuitry, based on the activity type in block 500. In addition, other reference information may be fed into the processing circuitry that may affect the selection of the subset, e.g. the attachment location of the wearable training computer (left/right hand). As described, the subset comprises antenna configurations that may be the most optimal for the selected activity type. The activity type may be, for example, running and then the subset comprises antenna configurations that are most suitable for the running associated with specific orientations, positions and movement of the wearable training computer. Hence, feeding in the activity type, the certain antenna configurations are preselected from the greater group of antenna configurations. Then the selection of the antenna configuration within the subset is done based on the actual measuring of the antenna performance made by the measuring circuitry 208. The processing circuitry may trigger the antenna measurements in block 502 and, as a consequence, the measurement circuitry 208 measures the RF properties of at least the currently selected antenna configuration and outputs the measured RF properties to the processing circuitry 206. In block 504, a decision is made by the processing circuitry 206 on the basis of the measured RF properties. The decision may be whether or not to maintain the current antenna configuration. If the current antenna configuration is maintained, the process may return to block 502 for another triggering of the (later) measurements. If the current antenna configuration is deemed sub-optimal, the processing circuitry may configure the RF switch 202 to implement a new antenna configuration of the subset. In other words, the processing circuitry 206 selects the optimal antenna configuration based on the antenna measurement data provided by the measuring circuitry 208. The antenna performance may be continuous process and hence the real-time antenna performance data is available for the processing circuitry to select the optimal configuration. In other words, the GNSS antenna of the wearable training computer is adaptive for the different orientations, positions and movement of the training computer during the activity.

In an embodiment, the processing circuitry is configured to change, based on the GNSS antenna performance measurement, the selected antenna configuration to the other antenna configuration as described in block 506. The antenna configuration selected from the subset of the antenna configurations may be changed to another configuration of the subset if the processing circuitry detects that the antenna performance of the selected configuration is not optimal. Hence, an initial selection of the antenna configuration may not be permanent. A default antenna configuration may be predefined as the initial antenna configuration. In another embodiment, the processing circuitry may employ machine learning and select, as the initial antenna configuration, an antenna configuration determined to provide the most suitable for variable conditions, e.g. an antenna configuration mostly used within the subset in the previous instants of the physical activity.

As described, the subset of the antenna configurations is selected based on the activity type and the antenna configuration is selected from the subset based on the antenna performance measurement. Hence, performance of the selected antenna configuration was optimal in that orientation and position of the wearable training computer when the measurement was performed. The orientation and position of the wearable training computer may change quickly and therefore, when the user of the wearable training computer change, for example, a position of the hand, the selected configuration is not necessarily optimal anymore. Then the measurement circuitry provides the measurement data that the configuration is not optimal and the processing circuitry may select the other configuration that may provide better performance. There may be, for example, a lower limit for the performance and, if the measured antenna performance goes below the limit, in other words, is worse that the set limit, the processing circuitry may change the antenna configuration. In case the performance of the all antenna configurations of the subset is below the limit, the processing circuitry may select the antenna configuration that provides the best performance, based on the measurements.

In an embodiment, the processing circuitry is configured to select an antenna configuration that provides the best performance within the subset. Hence, even though the performance of the selected antenna configuration would be better than the limit, it may still be changed if some other configuration is deemed to provide a better performance.

In an embodiment, the processing circuitry may select an antenna configuration outside the selected subset, if the antenna configuration is deemed to provide better performance. For example, if the processing circuitry detects that none of the antenna configurations of the selected subset cannot provide the optimal performance, the processing circuitry may try to find the antenna configuration from the greater group of antenna configurations than that of the initially selected subset. Upon finding a suitable antenna configuration, the processing circuitry may add the antenna configuration to the subset, thus avoiding degrading performance in the future.

In an embodiment, the processing circuitry is configured to change the selected antenna configuration during the activity of the user of the wearable training computer, wherein a plurality of the antenna configurations are used during the activity. As described earlier, the antenna configuration may be changed based on the performance measurement, if the performance of the selected antenna configuration is not sufficient or if an antenna configuration providing better performance is found. The change may be performed also during the activity, e.g. during a physical exercise. Normally the wearable training computer moves during the physical exercise. In other words, its orientation and position varies in relation to the user's body which may affect the performance of the antenna configuration. A first antenna configuration may be optimal in a first orientation and position of the wearable training computer but, most probably, the first antenna configuration is not optimal any more in a second orientation and position. Hence, the antenna configuration may be changed several times during the physical exercise, because of the changed orientation and position of the wearable training computer, to keep the antenna performance optimal. Hence, a plurality of antenna configurations may be used during the same physical exercise.

Figure 6:
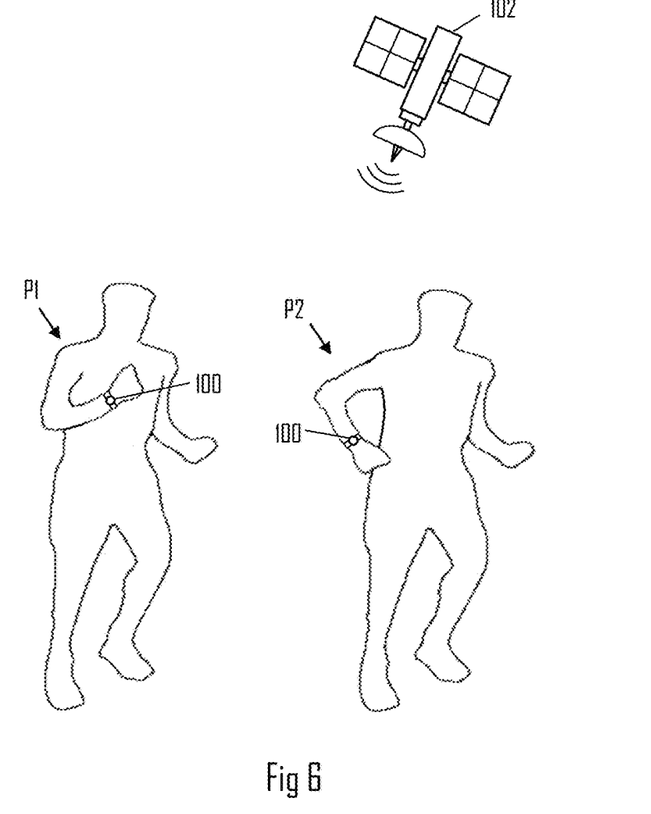
FIG. 6 illustrates motion and associated adaptation of antenna configurations according to an embodiment of the invention.

Referring to FIG. 6, let us describe an embodiment of using the wearable training computer 100. The wearable training computer may be worn in a right hand as illustrated in FIG. 6, and the wearable training computer may move during the activity such that there are at least two different positions in the movement. In the first position P1, the hand is front of the user and in the second position P2, the hand is behind the user. The orientation and position of the wearable training computer in relation to the user's body may be different in the positions. Hence, the same antenna configuration is not necessarily optimal in both positions, e.g. the user's body may shadow the antenna from the GNSS signal in position P2 while there may be a line-of-sight between the GNSS satellite 102 and the antenna in the position P1. Therefore, the antenna configuration may be changed when the position of hand is changed. For example, the first antenna configuration may be used in the first position P1 and the second antenna configuration may be used in the second position P2. Then the processing circuitry, based on the performance measurement, may change the antenna configuration between the first and second configurations, provided that the hand movement stays the same during the running. If further movement is made, further antenna configurations of the same subset may be employed by the processing circuitry. This is very simplified example and in a real physical exercise there would be a plurality of the positions of the wearable training computer and hence, also a plurality of the antenna configurations may be used.

In an embodiment, the processing circuitry is configured to detect a periodicity in a movement of the wearable training computer during the activity, and to select the antenna configuration based on the periodicity. Referring to the previous example and FIG. 6, wherein the movement of the wearable training computer comprises two different positions P1 and P2 during the running. The first antenna configuration may be used in the first position P1 and the second antenna configuration may be used in the second position P2. The processing circuitry may detect the periodicity in the movement, wherein the positions P1 and P2 are repeated successively, and the processing circuitry may select the antenna configuration based on the periodicity. Hence, the processing circuitry may define the used antenna configurations in advance based on the detected repeatability. For example, in the position P1 the first antenna configuration is used and when the processing circuitry detect that the antenna performance is weakening, it knows to change the first configuration to the second because it may suppose that position P2 comes after the position P1 because of the repeatability. Upon learning the periodicity, the processing circuitry may switch between the antenna (first and second) configurations with the same periodicity as the periodicity of the movement. The periodic switching may then be resumed even without making any performance measurements between consecutive switches. There may be, for example, a time limit for performing the periodic switching without measurements. For example, if the same positions are repeated longer than set time limit, the processing circuitry may trigger the measurements to ensure that the performance is still acceptable. The limit may also be a number of the repeated positions.

Accordingly, the processing circuitry may switch between at least two antenna configurations of the subset during each of a plurality of periods of the movement.

In the previous example, the motion and the periodicity of the motion may be detected by the processing circuitry by using a motion sensor comprised in the apparatus. The motion sensor may include an inertial measurement unit described below, or another motion sensor.

Still referring to the previous example, the processing circuitry may change the first antenna configuration to the second when the performance of the first configuration is not optimal anymore, for example, when the performance of the antenna configuration is below the set limit. Because of the detected repeatability in the movement, the processing circuitry may select automatically the second configuration when the first is not optimal anymore, even without the measurements. Thereafter, the measuring circuitry may still measure the antenna performance of the second antenna configuration and, if detected that it is not optimal, the processing circuitry may change the antenna configuration again, e.g. to another configuration that provides better performance.

In an embodiment, the wearable training computer further comprises an inertia measurement unit, IMU, configured to determine a position and/or an orientation of the wearable training computer, wherein the processing circuitry is configured to select, based on a feedback from the IMU, a subset of the antenna configurations from the group of the antenna configurations and/or the antenna configuration of the subset. The processing circuitry may associate certain positions and/or orientations with certain activity types, e.g. the position and orientation of the user's hand is different when preparing to run and when preparing to swim, thus enabling the selection of the subset. In an embodiment, the processing circuitry may determine the activity type based on the position and/or orientation and then, based on the determination, the subset of the antenna configuration is selected. For example, how and where the wearable training computer is worn affect the orientation and position, and this information may be applied when the processing circuitry is determining the activity type. In some embodiment, the subset of the antenna configurations may be created by the processing circuitry based on the information received from the IMU. The processing circuitry may determine, based on the orientation and position of the wearable training computer, which antenna configurations may be optimal to use and these configurations are then combined as a subset. In other words, the processing circuitry may not determine the activity type, it may just create the subset based on the antenna configuration that are most suitable for the orientation and positioning of the training computer.

In an embodiment, the motional feedback from the IMU is used also for selecting the antenna configuration from the subset. For example, when the wearable training computer is detected by the IMU to be in a specific position and/or orientation during the activity, the processing circuitry may select the antenna configuration based on the orientation and position. The processing circuitry may have predetermined data for defining which antenna configuration is optimal in the different positions and/or orientations. It is also possible that the optimal antenna configuration for the different positions and/or orientations is determined based on the measurements by the measurement circuitry. The measurement may have been performed earlier and measurement data saved, for example, in a database and used later in the configuration selection. Hence, the processing circuitry may be capable to connect the orientation and position data with the measurement data such that the processing circuitry may know which configuration may give the best performance in the certain position and orientation.

In an embodiment, the selection of the antenna configuration is done by the processing circuitry, based on the feedback from the IMU, and the performance of the selection is confirmed by the antenna performance measurement. For example, the IMU may give feedback for the processing circuitry about the position and orientation of the wearable training computer and based on the feedback the processing circuitry determines and selects the antenna configuration going to be used. The performance of the selected configuration is then confirmed by the measurement circuitry. Hence, the antenna configuration may be selected in a cooperation of the IMU, the processing circuitry and the measurement circuitry.

In an embodiment, the IMU comprises a gyroscope. The gyroscope is a motion sensor configured to measure rotational motion of the wearable training computer.

In an embodiment, the IMU comprises an accelerometer. The accelerometer is a motion sensor configured to measure acceleration along one, two, or three perpendicular directions.

In an embodiment, the IMU further comprises a magnetometer. The magnetometer is a motion sensor configured to measure motion on the basis of magnetic field measurements.

In the context of motion sensors, a sensor fusion may be employed, wherein the sensor fusion may be a combination of a three-dimensional accelerometer, a gyroscope, and a magnetometer. Sensor data measured by the sensor fusion may be combined to improve the accuracy of the motion sensing of the wearable training computer.

In an embodiment, the processing circuitry is configured to determine, based on an input of the user of the wearable training computer, the activity type of the user of the wearable training computer. The wearable training computer may comprise a selection of the different activity types and the user will select the activity he/she going to do. Based on the selection of the activity type, the processing circuitry may select the subset of the antenna configurations associated with the selected activity type in a memory of the training computer. The wearable training computer may further comprise a user interface. The user interface may comprise a display screen and input means such as buttons or a touch-sensitive display. The activity types may be shown on the screen to the user for making the selection of the activity. In an embodiment, the processing circuitry may preselect the activity types shown on the user interface based on the feedback from the IMU. For example, how and where the wearable training computer is worn may be used to define the activity types. Based on this, the wearable training computer may propose and show on the user interface the preselected group of the activity types and the user can make the selection. If the activity type is not among the proposed, the user can select also other activity types that may not be in the preselected group.

In an embodiment, the processing circuitry is configured to determine, based on a motion and/or location information of the wearable training computer, the activity type of the user of the wearable training computer. The GNSS is able to define a location of the wearable training computer and the location information may be used by the processing circuitry for selecting the activity type. For example, the user may perform a certain activity in a certain place, like for example running in an outdoor running track. The processing circuitry may recognize the location, for example, based on the previous activities and propose to select the running as an activity type. The previous activities means that the user has run in the same location earlier and the wearable training computer has this information. Hence, the training history saved on the database may be used when determining the activity type based on the location. In an embodiment, the user may also feed into the wearable training computer information about the activities and locations and based on this information the processing circuitry is able to connect the right location and the right activity type together. In some case, a plurality of activity types may be performed in the same location an hence, the processing circuitry may be capable to show the all activity types on the user interface and the user can then select the right activity.

In an embodiment, the processing circuitry is configured to determine, based on a training program saved on a database, the activity type of the user of the wearable training computer. The training program may be saved on the database where the processing circuitry have an access. The database may be, for example, a cloud service. The training program may define, for example, the activity type, a time for the activity and/or a location. In addition, many other attributes may be defined in the training program that can be utilized. The processing circuitry may be capable to utilize the information included in the training program. For example, the training program may define that Monday training is running, then the processing circuitry may automatically select the subset of the antenna configurations that are most suitable for running from the performance point of view. In some case, the wearable training computer may still ask the user to confirm that the activity type is running before the activity starts. Someday, there may be several training sessions in the program, for example, a first in the morning and a second in the evening, and the activity type of the sessions may be different. The processing circuitry may propose two different subsets wherein the first subset may be optimal for the first activity and the second subset for the second activity. The user can then select the right subset according to the activity he/she is going to do at that time. Time may also be used to separate different the training sessions. For example, the processing circuitry may recognize what time the each training session is and may then select the right subset for the right activity.

In an embodiment, a duration of the activity is also included in the training program that may be utilized, by the processing circuitry, when selecting the antenna configuration. As described earlier, the processing circuitry is capable to detect the repeatability in the movement of the wearable training computer and the repeatability may be used to predict the optimal antenna configuration. For example, the movement of the wearable training computer in the running may comprise two positions P1 and P2 as illustrated in FIG. 6. The processing circuitry is capable to detect that the position P1 and P2 are repeated systematically in the running. The processing circuitry may then automatically select the antenna configuration that is optimal for P2 when the performance of the antenna configuration used with the P1 getting weaker. In other words, the processing circuitry may predict based on the repeatability that P2 follows the P1 and the P1 follows the P2 and this information may be utilized in the antenna configuration selection. In addition, the duration of the activity may be applied. For example, the training program may define that the duration of the running is one hour. Then the processing circuitry may suppose that the positions P1 and P2 will be repeated one after another systematically for one hour. Even though the processing circuitry may select the antenna configuration based on the repeatability, the antenna configuration may be changed if the selected configuration, based on the prediction/repeatability, cannot provide an optimal antenna performance. For example, in case wherein the P2 does not follow the P1 for some reason.

In an embodiment, the measured performance of the GNSS antenna is defined in terms of a number of satellites detected by the GNSS receiver. The measuring circuitry is configured to define a number of the available satellites by communicating with the GNSS receiver. The number of the satellites is relative to the performance of the antenna configuration. The more satellites are detected, the better is the performance of the antenna configuration. For example, in some orientation and position of the wearable training computer, the minimum requirement of four satellites may be reached by the first antenna configuration but the second antenna configuration may reach a higher number of satellites, thus improving the positioning accuracy. Hence, the second antenna configuration may provide better performance and may be selected. In some case, a sufficient number of satellites may be detected with the first antenna configuration that provides high antenna performance and, at the same time, the second antenna configuration would reach even a higher number of satellites. However, the second antenna configuration may not be selected because the antenna performance provided by the first configuration is already good enough. Hence, it may not be necessary to change the configuration which is capable to achieve the optimal performance, even if there would be available a configuration that would provide higher performance.

In an embodiment, the performance of the GNSS antenna comprises signal-to-noise ratio, SNR, or one or more received GNSS signals. The measurement circuitry may be capable of measuring the SNR of the antenna configuration. The SNR compares a level of a desired signal to a level of background noise, it is defined as a ratio of signal power to the noise power. The orientation and position of the wearable training computer affects the SNR, and the antenna configuration that provides the best SNR may be selected by the processing circuitry based on the measurement data provided by the measurement circuitry.

The measured antenna performance may also comprise other attributes than mentioned number of the satellites and SNR. Also several different attributes may be combined when selecting the antenna configuration. Hence, the selection is not necessarily done based on only one attribute.

In an embodiment, the wearable training computer comprises one or more biometric sensors for measuring biometric data from the user of the wearable training computer. The biometric sensors may be attachable to an object such as a human body for use during a physical exercise and/or during daily routines. The biometrical sensors are used to measure the biometric data from the user's performance during the physical exercise and to output the data to the user via the user interface of the wearable training computer and/or another apparatus. The biometric data, measured by the biometric sensors, may comprise a biomedical and/or biomechanical data. The biometric data, measured from the user, may comprise, for example any of the following: heart rate, blood pressure, temperature, stress level and/or respiration rate. The biometric data is utilized to enable efficient training.

In an embodiment, the one or more biometric sensors comprise one or more electrodes. The electrodes are utilized in the heart activity measurement, like an electrocardiogram (ECG), wherein the electrodes are attached to the user's skin for measuring the ECG-signal.

In an embodiment, the one or more biometric sensors comprise one or more optical sensors. The heart activity may also be measured by the optical sensors. The optical sensors are used in a photoplethysmogram (PPG) in which the optical sensor may detect the heart activity of the user by an optical measurement.

In some embodiment, different sensors may be combined in the wearable training computer to measure desired biometric data from the user.

The next example describes how the invention may be applied in use. The wearable training computer may comprise a group of the antenna configurations having different RF-properties. A plurality of the antenna configurations are needed to cover the different orientation and position of the wearable training computer. At first, the subset of the antenna configurations is selected from the group of the antenna configurations. The selection is made, for example, before triggering biometric measurements for the activity type such as the physical exercise. When the selection of the subset is done, an initial antenna configuration is selected based on the antenna performance measurement. The initial antenna configuration may also be selected before starting the biometric measurements. Thereafter, the activity and associated biometric measurements may be triggered. Meanwhile, the measuring circuitry measures the antenna performance, for example, continuously or repeatedly. The orientation and position of the wearable training computer changes all the time during the activity and hence, the antenna configuration may also be changed to maintain the optimal antenna performance. The wearable training computer selects the configuration which is capable to provide the optimal antenna performance for the current orientation and position of the wearable training computer. The antenna configuration is selected from the subset and its performance is ensured by the measurement. It may also be possible to select the configuration out of the selected subset if needed. This enables the adaptive antenna system which performance is always optimal nevertheless the orientation and position of the wearable training computer is changing all the time.

Figure 7:
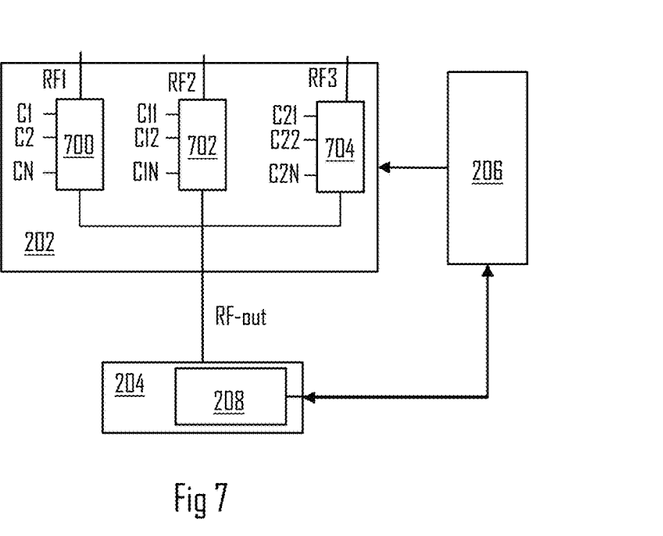
FIG. 7 illustrates an embodiment of FIG. 2.

As described above, the RF switch 202 may be controlled by the processing circuitry 206 to implement the antenna configuration. FIG. 7 illustrates an embodiment where the RF switch comprises a separate switch 700, 702, 704 for each RF contact point RF1, RF2, RF3. Each of the switches 700 to 704 may be controlled to couple the contact point to the ground, the antenna feed, or the open end either directly or through a circuitry denoted by reference signs C1, C2, CN, C11, C12, C1N, C21, C22, C2N. As described above, this expands the number of antenna configurations available to the processing circuitry. A circuitry connectable by the switches 700 to 704 may comprise one or more RF components such as a capacitor, inductor, resistor, or an RF reflector. The RF reflector may reflect the GNSS signal, and the different antenna configurations may affect the RF properties of the antenna, depending on whether or not the reflector is employed.

In an embodiment, the processing circuitry is configured to associate one or more antenna configurations with operational parameters of the GNSS receiver. As a consequence, upon selecting an antenna configuration the processing circuitry may output a control signal to the GNSS receiver to change the operational parameters to match with the selected antenna configuration. The operational parameters may include parameters of a low-noise amplifier and/or an RF filter of the GNSS receiver, for example. Accordingly, a further capability for adapting the performance of the GNSS reception to the motion of the user may be achieved.

As used in this application, the term 'circuitry' refers to all of the following: (a) hardware-only circuit implementations, such as implementations in only analog and/or digital circuitry, and (b) combinations of circuits and software (and/or firmware), such as (as applicable): (i) a combination of processor(s) or (ii) portions of processor(s)/software including digital signal processor(s), software, and memory(ies) that work together to cause an apparatus to perform various functions, and (c) circuits, such as a microprocessor(s) or a portion of a microprocessor(s), that require software or firmware for operation, even if the software or firmware is not physically present. This definition of 'circuitry' applies to all uses of this term in this application. As a further example, as used in this application, the term 'circuitry' would also cover an implementation of merely a processor (or multiple processors) or a portion of a processor and its (or their) accompanying software and/or firmware.

The techniques and methods described herein may be implemented by various means. For example, these techniques may be implemented in hardware (one or more devices), firmware (one or more devices), software (one or more modules), or combinations thereof. For a hardware implementation, the apparatus(es) of embodiments may be implemented within one or more application-specific integrated circuits (ASICs), digital signal processors (DSPs), digital signal processing devices (DSPDs), programmable logic devices (PLDs), field programmable gate arrays (FPGAs), graphics processing units (GPUs), processors, controllers, micro-controllers, microprocessors, other electronic units designed to perform the functions described herein, or a combination thereof. For firmware or software, the implementation can be carried out through modules of at least one chipset (e.g. procedures, functions, and so on) that perform the functions described herein. The software codes may be stored in a memory unit and executed by processors. The memory unit may be implemented within the processor or externally to the processor. In the latter case, it can be communicatively coupled to the processor via various means, as is known in the art. Additionally, the components of the systems described herein may be rearranged and/or complemented by additional components in order to facilitate the achievements of the various aspects, etc., described with regard thereto, and they are not limited to the precise configurations set forth in the given figures, as will be appreciated by one skilled in the art.

It will be obvious to a person skilled in the art that, as the technology advances, the inventive concept can be implemented in various ways. The invention and its embodiments are not limited to the examples described above but may vary within the scope of the claims.

What is claimed is:

1. A wearable training computer, comprising:
   a global navigation satellite system (GNSS) antenna arrangement configured to provide a first plurality of antenna configurations for receiving a GNSS signal, wherein each antenna configuration provides different radio frequency properties;
   a measurement circuitry configured to measure performance of the GNSS antenna to provide signal quality data between an antenna configuration of the GNSS antenna arrangement and one or more GNSS satellites; and
   a processing circuitry configured to process the signal quality data, to select, based on at least an activity type of a user of the wearable training computer, a subset of the antenna configurations from the first plurality of the antenna configurations, the subset of the antenna configurations comprising a second plurality of antenna configurations that is less than the first plurality of antenna configurations, and the processing circuitry being further configured to select, from the subset of the antenna configurations based on real-time measured GNSS antenna performance from the signal quality data, an antenna configuration for receiving the GNSS signal.

2. The wearable training computer of claim 1, wherein the processing circuitry is configured to change, based on the GNSS antenna performance measurement, the selected antenna configuration to another antenna configuration of the subset.

3. The wearable training computer of claim 1, wherein the processing circuitry is configured to detect periodicity in a movement of the wearable training computer during the activity, wherein the processing circuitry is further configured to select the antenna configuration based on the detected periodicity.

4. The wearable training computer of claim 3, wherein the processing circuitry is configured to change the antenna configuration periodically with the same periodicity as the detected periodicity of the movement.

5. The wearable training computer of claim 4, wherein the processing circuitry is configured to switch between at least two antenna configurations of the subset during each of a plurality of periods of the movement.

6. The wearable training computer of claim 1, wherein the wearable training computer further comprises an inertia measurement unit (IMU) configured to determine at least one of a position and an orientation of the wearable training computer, wherein the processing circuitry is further configured to select, based on the at least one of the position and the orientation, the antenna configuration.

7. The wearable training computer of claim 6, wherein the IMU comprises at least one of a gyroscope, an accelerometer, and a magnetometer.

8. The wearable training computer of claim 1, wherein the processing circuitry is configured to determine, based on an input of the user of the wearable training computer, the activity type of the user of the wearable training computer.

9. The wearable training computer of claim 1, wherein the processing circuitry is configured to determine, based on a location information of the wearable training computer, the activity type of the user of the wearable training computer.

10. The wearable training computer of claim 1, wherein the processing circuitry is configured to determine, based on a training program saved on a database, the activity type of the user of the wearable training computer.

11. The wearable training computer of claim 1, wherein the performance of the GNSS antenna comprises a number of detected GNSS satellites.

12. The wearable training computer of claim 1, wherein the performance of the GNSS antenna comprises signal-to-noise ratio (SNR) of a received GNSS signal.

13. The wearable training computer of claim 1, wherein the wearable training computer comprises one or more biometric sensors for measuring biometric data from the user of the wearable training computer while the user performs activities of the activity type.

14. The wearable training computer of claim 1, wherein the activity type is a sports type incorporating GNSS positioning of the wearable training computer.

15. The wearable training computer of claim 1, wherein the antenna arrangement comprises:
   a GNSS antenna;
   a radio frequency switch with multiple contact points to a GNSS antenna; and
   a GNSS signal processing circuitry configured to process a received GNSS signal,
   wherein the radio frequency switch is configured, under the control of the processing circuitry to interchangeably couple each of the contact points to one or more of the GNSS signal processing circuitry, ground, and open to realize the first plurality of antenna configurations.

* * * * *